United States Patent
Ciocan et al.

(10) Patent No.: US 7,725,167 B2
(45) Date of Patent: May 25, 2010

(54) MICROWAVE IMAGING ASSISTED ULTRASONICALLY

(75) Inventors: Razvan M. Ciocan, Central, SC (US); Huabei Jiang, Gainesville, FL (US)

(73) Assignee: Clemson University, Anderson, SC (US)

( * ) Notice: Subject to any disclaimer, the term of this patent is extended or adjusted under 35 U.S.C. 154(b) by 1133 days.

(21) Appl. No.: 11/180,434

(22) Filed: Jul. 13, 2005

(65) Prior Publication Data

US 2007/0015993 A1    Jan. 18, 2007

(51) Int. Cl.
*A61B 5/05* (2006.01)
*A61B 8/00* (2006.01)

(52) U.S. Cl. .................. 600/430; 600/438; 600/449
(58) Field of Classification Search ............... 600/430, 600/437, 438, 449; 601/2
See application file for complete search history.

(56) References Cited

U.S. PATENT DOCUMENTS

| | | | | | |
|---|---|---|---|---|---|
| 4,597,293 | A | * | 7/1986 | Kanda et al. | 73/606 |
| 4,870,423 | A | * | 9/1989 | Bolomey | 342/368 |
| 5,115,673 | A | * | 5/1992 | Kline et al. | 73/601 |
| 5,715,819 | A | | 2/1998 | Svenson et al. | |
| 5,841,288 | A | * | 11/1998 | Meaney et al. | 324/639 |
| 5,957,851 | A | * | 9/1999 | Hossack | 600/459 |
| 6,448,788 | B1 | | 9/2002 | Meaney et al. | |
| 6,490,470 | B1 | * | 12/2002 | Kruger | 600/407 |
| 6,567,688 | B1 | * | 5/2003 | Wang | 600/430 |
| 2005/0107692 | A1 | * | 5/2005 | Li et al. | 600/430 |

OTHER PUBLICATIONS

Article—*The quality evaluation of the end-plate welds and brazed joints for CANDU nuclear fuel by an ultrasonic imaging method*, Ciocan, et al., Insight, vol. 39, No. 9, Sep. 1997, pp. 622-625.
Article—*Medical Imaging with a Microwave Tomographic Scanner*, Jofre, et al., IEEE Transactions on Biomedical Engineering, vol. 37, No. 3, Mar. 1990, pp. 303-311.
Article—*Microwave Imaging Techniques for Biomedical Applications*, Joisel, et al., IEEE, Sep. 1999, pp. 1591-1596.
Article—*Quantitative Microwave Imaging with a 2.45-GHz Planar Microwave Camera*, Franchois, et al., IEEE Transactions on Medical Imaging, vol. 17, No. 4, Aug. 1998, pp. 550-561.
Article—*Inverse Scattering: An Iterative Numerical Method for Electromagnetic Imaging*, Joachimowicz, et al., IEEE Transactions on Antennas and Propagation, vol. 39, No. 12, Dec. 1991, pp. 1742-1752.
Article—*An Active Microwave Imaging System for Reconstruction of 2-D Electrical Property Distributions*, Meaney, et al., IEEE Transactions on Biomedical Engineering, vol. 42, No. 10, Oct. 1995, pp. 1017-1026.

(Continued)

*Primary Examiner*—Eric F Winakur
*Assistant Examiner*—Michael T Rozanski
(74) *Attorney, Agent, or Firm*—Dority & Manning, P.A.

(57) ABSTRACT

Disclosed is an apparatus and methodology for imaging objects, more particularly radiologically dense objects. The currently disclosed technology has particular applicability in the medical field as a tool and methodology for investigation of radiologically dense breast tissue of young patients by using microwave energy in concert with an ultrasonic initial investigation of the tissue. The use of an ultrasonic initial investigation operates as an initial evaluation point for the subsequent microwave investigation.

15 Claims, 7 Drawing Sheets

OTHER PUBLICATIONS

Article—*Three-Dimensional Microwave Tomography. Theory and Computer Experiments in Scalar Approximation*, Bulyshev, et al., Inverse Problems 16 (2000), pp. 863-875.

Article—*A contrast source inversion method*, van den Berg, et al., Inverse Problems 13 (1997), pp. 1607-1620.

Abstract of Article—*Computational modeling of three-dimensional microwave tomography of breast cancer*, Bulyshev et al., IEEE Trans. Biomed. Eng., vol. 48, No. 9, Sep. 2001, pp. 1053-1056.

Abstract of Article—*Convergence and stability assessment of Newton-Kantorovich reconstruction algorithms for microwave tomography*, Joachimowicz et al., IEEE Trans. Med. Imaging, vol. 17, No. 4, Aug. 1998, pp. 562-570.

Abstract of Article—*Pre-scaled two-parameter Gauss-Newton image reconstruction to reduce property recovery imbalance*, Meaney et al., Phys. Med. Biol., vol. 47, No. 7, Apr. 7, 2002, pp. 1101-1119.

Abstract of Article—*Three-dimensional nonlinear image reconstruction for microwave biomedical imaging*, Zhang et al., IEEE Trans. Biomed. Eng., vol. 51. No. 3, Mar. 2004, pp. 544-548.

Article—*Microwave Imaging Using the Finite-Element Method and a Sensitivity Analysis Approach*, Rekanos et al., IEEE Transactions on Medical Imaging, vol. 18, No. 11, Nov. 1999, pp. 1108-1114.

Article—*Microwave scattering parameter imagery of an isolated canine kidney*, Medical Physics, vol. 6, No. 5, Sep./Oct. 1979, pp. 394-403.

Article—*Model-based microwave image reconstruction: simulations and experiments*, Ciocan et al., Medical Physics, vol. 31, No. 12, Dec. 2004, pp. 3231-3241.

\* cited by examiner

MICROWAVE IMAGING ASSISTED ULTRASONICALLY

FIELD OF THE INVENTION

The present subject matter relates to imaging using microwave radiation. More particularly, the present subject matter relates to the production of a representation of electric permittivity and conductivity in a test object, the production of such representation being assisted through the use of an ultrasonic initialization technique. The present subject matter has applicability in the medical arts as an adjunct to, or replacement for, x-ray mammography.

BACKGROUND OF THE INVENTION

Presently available information indicates the following: 1) More than 211,000 American women will be diagnosed with breast cancer this year; 2) Ninety two percent of late-stage breast cancer cases in the United States could have been treated if they had been detected earlier; 3) About 70 percent of women over 40 years of age had a mammogram in the last two years; 4) Mammography, in spite of its unpleasant procedure for women (breast constriction) and its radiation exposure problems, remains the only method available for breast cancer detection; and 5) Mammography shows a high rate of failure for women in the 25 to 40 year old age group who tend to have radiological dense breast.

Recently there has been considerable interest in developing alternative methods for breast cancer detection due to the inability of x-ray mammography to image radiological dense breasts as well as the low positive predictive value in such circumstances. Among various alternative methods, microwave imaging is of particular clinical interest because of the high contrast available at microwave frequencies between normal and malignant tissues. One comparative study showed that microwave imaging could offer an order of magnitude higher contrast than x-ray or ultrasound imaging techniques.

The earliest work in microwave imaging for biomedical applications known to the preset inventors was a study by Larsen and Jacobi entitled "Microwave Scattering Parameter Imagery of an Isolated Canine Kidney" (Medical Physics—September 1979—Volume 6, Issue 5, pp. 394-403). Their work was conducted at 3.9 GHz using scanning for imaging isolated organs. The microwave images they obtained showed that exact anatomy cannot be recovered but contours related to lobular organization were identifiable. These disadvantages, however, have been overcome in part through the use of reconstructive algorithms.

A first type of reconstruction algorithm, known as a Born approximation, used in microwave imaging is based on the assumption of weak scatters and is referred to as diffraction tomography. The main advantage of this algorithm is that it provides a quasi real-time reconstruction of the polarization current density distribution. Microwave images obtained based on diffraction algorithms are able to provide qualitative information about objects under investigation but they fail to provide qualitative images of electric properties, i.e. permittivity and conductivity, of object with high contrast. This failure results from an initial assumption that does not take into consideration multiple scattering but rather assumes the reconstruction problem to be a linear problem.

To consider multiple scattering, an iterative nonlinear algorithm must be used. At each iteration, an equation, e.g. a Helmholtz equation, describing electric field distribution in homogeneous media is solved. Then the electric properties are adjusted by minimizing the errors between measured and calculated electric fields. This procedure takes into account nonlinearity of the inverse scattering problem eliminating the contrast limitation of diffraction tomography as well as allowing resolution better than half wavelength to be achieved. The ultimate factors that determine the resolution of a nonlinear algorithm are the available signal-to-noise ration (SNR) and accuracy in evaluation of electric field.

Prior nonlinear reconstruction approaches have been developed including: Newton-type with Tikhonov regularization as described by Joachimowicz et al. in their article "Inverse scattering: an iterative numerical method for electromagnetic imaging," IEEE Transactions on Antennas and Propagation, 1991 and by Joachimowicz et al. in their article "Convergence and Stability Assessment of Newton-Kantorovich Reconstruction Algorithms for Microwave Tomography," IEEE Transactions on Medical Imaging, 1998; Newton-type with Marquardt regularization as described by Meaney et al. in their article "An active microwave imaging system reconstruction of 2-D electrical property distributions," IEEE Transactions on Biomedical Engineering, 1995 and by Meaney et al. in their article "Pre-scaled two-parameter Gauss-Newton image reconstruction to reduce property recovery imbalance," Physics in Medicine and Biology, April 2002; conjugate-gradient with Tikhonov regularization as described by Rekanos et al. in their article "Microwave imaging using the finite-element method and a sensitive analysis approach," IEEE Transactions on Medical Imaging, 1999 and by Bulyshev et al. in their article "Computational modeling of three-dimensional microwave tomography of breast cancer," IEEE Transactions on Biomedical Engineering," 2001; and contrast source inversion methods as described by van den Berg et al. in their article "A contrast source inversion method," Inverse Problems, 1997 and by Zhang et al, in their article "Three-dimensional nonlinear image reconstruction for microwave biomedical imaging," IEEE Transactions on Biomedical Engineering, 2004.

While various implementations of microwave image reconstruction have been developed, and while various data refining algorithms have been devised, no design has emerged that generally encompasses all of the desired characteristics as hereafter presented in accordance with the subject technology.

SUMMARY OF THE INVENTION

In view of the recognized features encountered in the prior art and addressed by the present subject matter, an improved methodology for microwave image reconstruction has been developed.

The present subject matter relates to a method and a system for determining the local distribution of electric permittivity and conductivity of an object under investigation based on microwave measurements assisted ultrasonically. Initially, scanning ultrasonic measurements are made using ultrasonic transducers operated in reflection mode to determine the contour of an object being examined. Information regarding position of local disturbance in elastic properties is also obtained in this ultrasonic investigation. Any plane identified ultrasonically to contain an abnormal distribution of elastic properties may then be investigated using electromagnetic field at microwave frequencies.

Multiple antennas surround the object under investigation. The antenna design, their position and coupling medium assure a uniform electric field pattern in coronal plane of object under investigation. At a certain instant one of the antennas plays the role of the emitter and the other antennas operate as receivers. The amplitude and phase of electric field are measured for each location and for each configuration of individual emitter and multiple receivers. A second microwave measurement is performed without a target (homogeneous case) and the results of this measurement are used to calibrate the microwave data obtained during the object investigation (nonhomogeneous case). This calibration is needed to minimize several differences existing between the experimental system and the numerical models used, including: 1) the 3D imaging system and the 2D numerical models; 2) differences in transmission efficiency of antennas and connection cables; and 3) differences in the antenna positioning.

The local distribution of electric permittivity (er) and conductivity (s) is obtained based on experimentally calibrated data using a so called reconstruction algorithm. In the first step of this algorithm the electric field in each point of the investigated area is computed assuming a certain distribution for er and s. This assumption, called an initial guess, is based on information obtained during the ultrasound investigation. Values of the electric field computed using this initial distribution are compared with the experimental values. If error between calibrated measured field and computed field is not sufficiently small, the values for er and s are modified and new values for electric field are computed. This process is repeated until a stable solution is reached.

In an exemplary embodiment of the present subject matter, the reconstruction algorithm was implemented using a Newton iterative method with combined Marquardt-Tikhonov regularizations. The electric field at each iteration was computed using a finite element formulation of Bayliss and Turkel radiation boundary conditions. The approach using a hybrid regularizations-based Newton method to update an initial dielectric property distribution iteratively in order to minimize an object function composed of a weighted sum of the squared difference between computed and measured data may provide a more stable inverse solution than previously available.

In one form, the algorithm in accordance with the present subject matter uses a finite element method to solve for the Helmholtz equation subject to the Bayliss and Turkel radiation boundary condition (RBC) as described in their article "Radiation boundary conditions for wavelike equations", Commun. Pure Appl. Math., XXXIII, 707, (1980), to obtain the computed electric field data.

In accordance with certain aspects of other embodiments of the present subject matter, methodologies have been developed to make possible effective imaging of the radiologically dense breasts of younger women thereby providing greater opportunity for early detection of breast cancer in younger patients.

Additional objects and advantages of the present subject matter are set forth in, or will be apparent to, those of ordinary skill in the art from the detailed description herein. Also, it should be further appreciated that modifications and variations to the specifically illustrated, referred and discussed features and elements hereof may be practiced in various embodiments and uses of the invention without departing from the spirit and scope of the subject matter. Variations may include, but are not limited to, substitution of equivalent means, features, or steps for those illustrated, referenced, or discussed, and the functional, operational, or positional reversal of various parts, features, steps, or the like.

Still further, it is to be understood that different embodiments, as well as different presently preferred embodiments, of the present subject matter may include various combinations or configurations of presently disclosed features, steps, or elements, or their equivalents (including combinations of features, parts, or steps or configurations thereof not expressly shown in the figures or stated in the detailed description of such figures). Additional embodiments of the present subject matter, not necessarily expressed in the summarized section, may include and incorporate various combinations of aspects of features, components, or steps referenced in the summarized objects above, and/or other features, components, or steps as otherwise discussed in this application. Those of ordinary skill in the art will better appreciate the features and aspects of such embodiments, and others, upon review of the remainder of the specification.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which:

FIGS. 5a and 5b are comparative representative reconstructed permittivity images for a phantom with a small inclusion where

Repeat use of reference characters throughout the present specification and appended drawings is intended to represent same or analogous features or elements of the invention.

DETAILED DESCRIPTION OF THE PREFERRED EMBODIMENTS

As discussed in the Summary of the Invention section, the present subject matter is particularly concerned with an improved methodology for microwave image reconstruction of primarily, but not exclusively, breast tissue for medical evaluation of the possible presence of cancer. More particularly, the present subject matter concerns the provision and use of an initial evaluation point or "guess" for a microwave investigation based on the results of an initial ultrasound investigation.

Selected combinations of aspects of the disclosed technology correspond to a plurality of different embodiments of the present invention. It should be noted that each of the exemplary embodiments presented and discussed herein should not insinuate limitations of the present subject matter. Features or steps illustrated or described as part of one embodiment may be used in combination with aspects of another embodiment to yield yet further embodiments. Additionally, certain features may be interchanged with similar devices or features not expressly mentioned which perform the same or similar function. Reference will now be made in detail to the presently preferred embodiments of the subject microwave imaging system.

Figure 1:
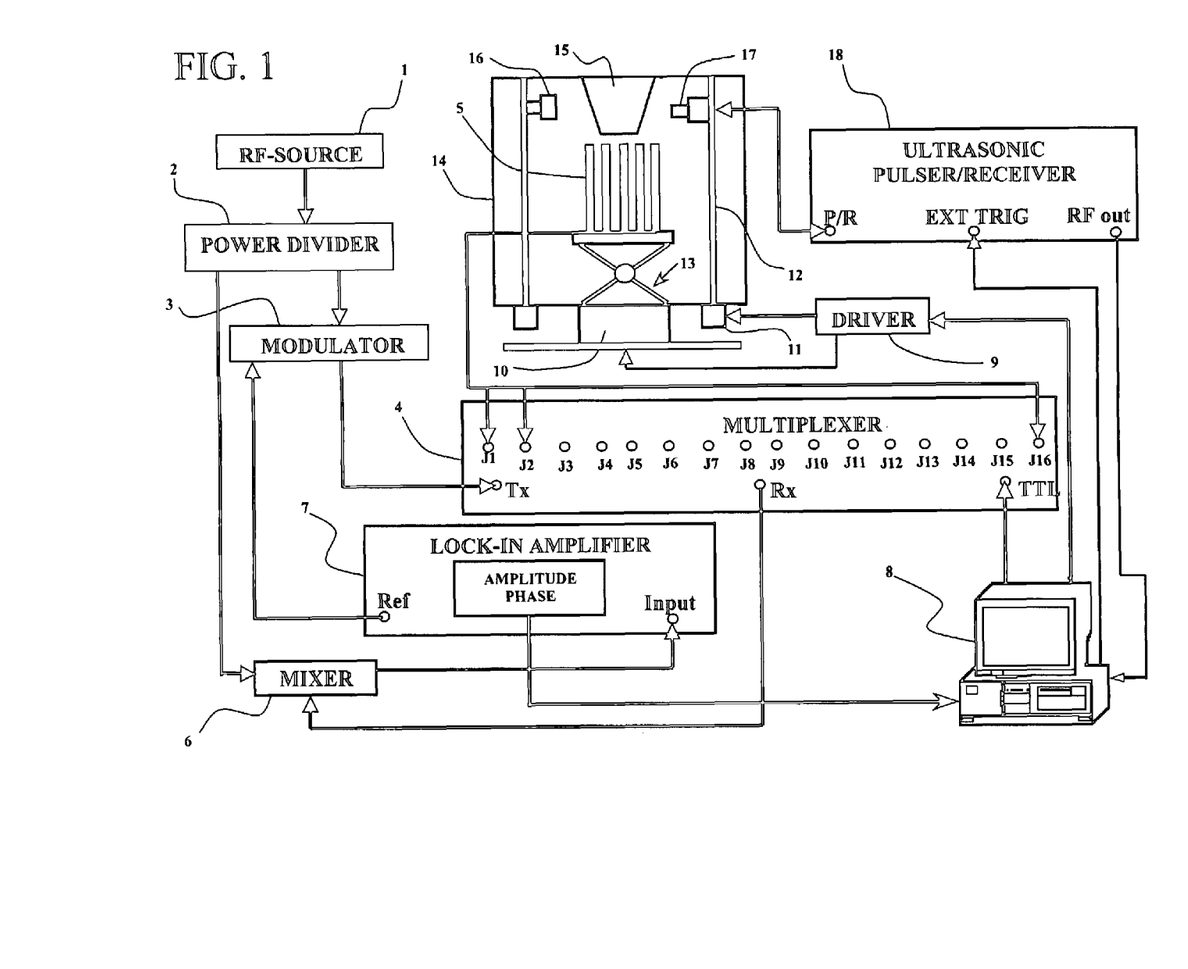
FIG. 1 illustrates a functional block diagram for an exemplary system constructed according to the preset subject matter.

Referring now to the drawings, FIG. 1 illustrates a block diagram for an exemplary system constructed according to the preset subject matter. The illustrated system may be used to obtain microwave images of body portions 15 of human subjects. It should be borne in mind that, although the principle portion of the present disclosure is directed to imaging of breast tissue, the present subject matter is not limited to such as the technology disclosed may also be used to image other tissue as well.

Apparatus constructed according to the present subject matter provides an ultrasound transducer 17 immersed in water tank 14. A stainless steel target 16 is positioned opposite the ultrasound transducer 17 and provides a reflected signal to assist both in the accurate determination of ultrasonic speed in the coupling medium and in the deconvolution process. So as not to overly clutter the drawing, only a single ultrasound transducer 17 and stainless steel target 16 have been illustrated, but it should be appreciated that plural transducers or a transducer array might be employed to reduce the scanning time required for imaging.

Exciting ultrasonic transducer 17 with a square wave signal emitted by an ultrasonic pulser/receiver (transceiver) 18 initiates the imaging process. The full waveform received by the ultrasound transducer 17 may be saved in any convenient format including both analog and digital forms for post-processing. Ultrasonic scanning investigations may be performed by rotating water tank 14 using a computer-controlled rotator 10 and by providing vertical movement of ultrasound transducer 17 and target 16 using linear stages 12. This translational movement may be performed manually or can be accomplished with computer assistance. As noted previously, instead of a single transducer, several discrete transducers or array transducers can be used in order to decrease the scanning time.

The scanning ultrasound as described above is used to investigate successive coronal planes of breast tissue. A quasi-real time ultrasound image of investigated planes is obtained that may be employed to detect the presence of suspicious inhomogeneities. If such inhomogeneities are detected, the ultrasound assembly may be lowered to make room for the microwave imaging system. The plane within the object under investigation containing suspicious inhomogeneities located using ultrasound and, optionally also, one or more planes on one or both sides of the plane may then be microwave imagined.

The ultrasound system corresponding to ultrasound transducer 17 and associated pulser/receiver 18 allows retrieval of full information regarding elastic properties distribution of investigated tissue. A data acquisition board operating at a 100 MHz sampling rate may be associated with computer 8 and used to save the full waveform of the received ultrasound signal at each scanning point. Having this information available, techniques that are currently used in ultrasound imaging can be applied to obtained high quality ultrasound images. These techniques include, but are not limited to, acoustic impedance profiling and second harmonic imaging.

Acoustic impedance profiling of the investigated tissue is a post-acquisition process primarily involving a deconvolution followed by a filtering of the RF signal received. Second harmonic ($2f_o$) ultrasound images are ultrasonic images obtained based on second harmonic ($2f_o$) signals and are characterized by a higher resolution than those obtained at the primary frequency $f_o$ as the second harmonic ultrasound beam is narrower than at those obtained at primary frequency ($f_o$). The ability to obtain a high-resolution ultrasonic image is an important aspect of an ultimate goal of obtaining an improved microwave reconstruction.

The microwave-imaging configuration employed in accordance with the present subject matter is similar to those configurations used in continuous wave radar detection. A fully programmable radio frequency (RF) source 1 provides a reference continuous RF signal. Power divider 2 separates the signal provided by RF source 1 in two portions. A first portion is coupled to modulator 3 and becomes the modulated signal to be transmitted by antenna array 5. A second portion of the RF signal provided by RF source 1 is coupled as one input to mixer 6 where it multiplies the received signal provided by multiplexer 4. The resultant signal from mixer 6 constitutes the input signal for lock-in amplifier 7. Amplitude and phase data from lock-in amplifier 7 are sent to computer 8 that controls all aspects related to data acquisition and signal conditioning by way of a user-friendly interface.

The user-friendly interface corresponds to a software package specifically developed for use with the subject microwave imaging technology. The software is configured to provide various functions including generating all voltages necessary for multiplexer control, performing data acquisition from lock-in amplifier, controlling a high speed data acquisition board used for the initial ultrasound investigation, controlling necessary mechanical movement for the ultrasound and microwave assemblies, and providing real time plotting and averaging for acquired data.

The microwave investigation portion of the system according to the present subject matter corresponds, along with the previously described RF source and related components, to an array of sixteen antennas fixed on an antenna holder 5. It should be appreciated that the exact number of antenna elements provided may be varied and may correspond to more or less than the exemplary discussed sixteen antennas. Antenna holder 5 is configured to provide a number of features including holding the antenna elements in place, protecting connection points between individual antennas and their associated connecting cables from the salty water employed as a coupling medium within the water tank 14, and providing a mechanical base for translation of the antenna array. In an exemplary embodiment of the present subject matter, the antenna assembly may be moved using a stainless steel jack. In an alternate embodiment of the present subject matter, a pair of computer controlled linear stages may be used as an alternative to move the antenna array as required for the imaging process.

Amplitude and phase information of transverse mode (TM) electric fields received from antennas positioned on a circle surrounding the area to be investigated constitute the input data for the microwave imaging according the present subject matter. In an exemplary embodiment of the present subject matter, sixteen antennas were employed. As previously noted, however, this specific number of antennas is not a limitation of the present subject matter. During the data collection process, each of the individual antennas in sequence is operated as a transmitter while the remaining antennas function as receivers. Each of the antennas is sequentially operated as the transmitting antenna such that a total of 240 measurements are obtained in an exemplary reconstruction process using sixteen antennas ($16 \times 15 = 240$). In accordance with the present subject matter, two microwave images are obtained as result of each investigation. These images are obtained as a result of a reconstruction process and are displayed as maps of the relative permittivity and conductivity of the investigated object. The inverse solution employed in the reconstruction process is based on the approximation that the true electric field, $E_{true}$, can be Taylor expanded around an approximate electrical profile, $E_{approx}$, as a function of the dielectric properties:

$$E_{true}(\varepsilon_r, \sigma) \cong E_{approx}(\varepsilon_r, \sigma) + \frac{\partial E_{approx}}{\partial \varepsilon_r}\Delta\varepsilon_r + \frac{\partial E_{approx}}{\partial \sigma}\Delta\sigma \qquad (1)$$

$$\Phi_{E_{true}}(\varepsilon_r, \sigma) \cong \Phi_{E_{approx}}(\varepsilon_r, \sigma) + \frac{\partial \Phi_{E_{approx}}}{\partial \varepsilon_r}\Delta\varepsilon_r + \frac{\partial \Phi_{E_{approx}}}{\partial \sigma}\Delta\sigma \qquad (2)$$

where E is the electric field, $\Phi_E$ is electric field phase, and $\epsilon_r$ and $\sigma$ are the permittivity and conductivity, respectively.

Figure 2:
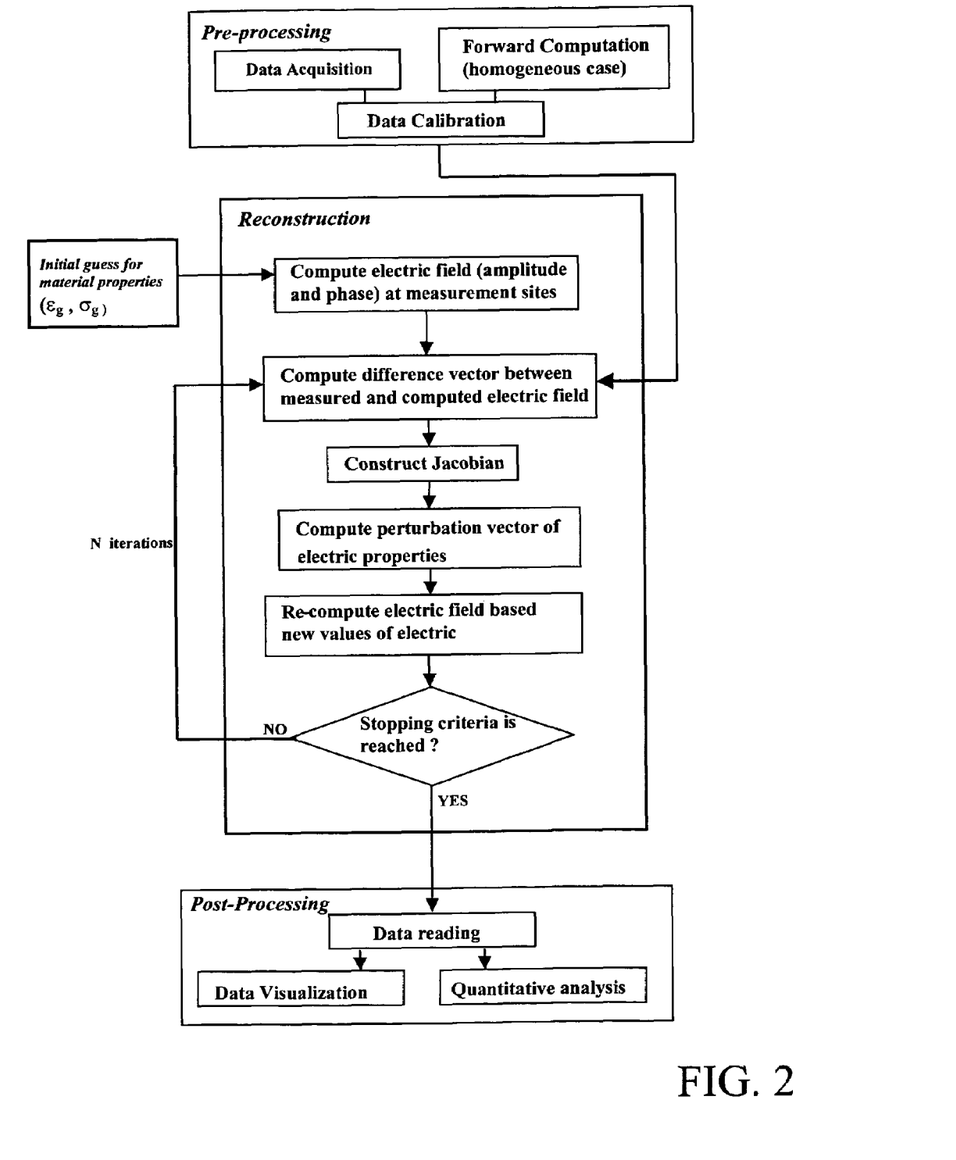
FIG. 2 is a flow chart illustrating exemplary steps to be taken to obtain a microwave image using the preset subject matter.

With reference now to FIG. 2, there are illustrated exemplary steps employed to obtain a microwave image using apparatus and methodologies according to the present subject matter. An exemplary reconstruction algorithm in accordance with the present subject matter can be summarized as corresponding to a five-step process.

A first step in the exemplary reconstruction algorithm corresponds to computing the amplitude and phase of electric field at measurement sites based on an initial guess for material properties ($\epsilon_g$, $\sigma_g$). According to the present subject matter, this initial guess is based on ultrasound-recovered profiles and is obtained using an algorithm based on so called Bayliss and Turkel Radiation Boundary Condition.

A main step in reconstruction of permittivity and conductivity profiles based on experimental data corresponds to a so-called forward or direct computation step. The numerical evaluation of the amplitude and phase of an electric field in a region $\Gamma$ is performed in this step based on a knowledge of the distribution of electrical properties (permittivity and conductivity) in the region, the radiation source position on the region boundary ($\partial\Gamma$), and the amplitude, phase and polarization characteristics of the radiation source.

According to the present subject matter, a Finite Element Method (FEM) may be applied to solve the forward problem. In such a formulation the forward problem is reduced from one of solving a hyperbolic partial differential equation to one of matrix algebra. The finite element formulation requires a division of the region $\Gamma$ into regions of constant permittivity and permeability. Triangle elements were considered for this application. If $\Gamma$ is divided in a mesh that contains $N_e$ elements and n nodes, the electric field may be written as:

$$E_z = \sum_{i=1}^{n}(E_z)_i \Psi_i \qquad (3)$$

where: $\Psi_i$ is the basis function centered at node "i" and $(E_z)_i$ represents the interpolated value of $E_z$ at node "i". Quantities at each node represent the vector components. By multiplying both sides of the wave equation with a test function $\psi(x,y)$ and performing integration over $\Gamma$ the weak form of the wave equation is obtained:

$$\int\int\left(\nabla\Psi\left(\frac{1}{\mu_r}\nabla E_z\right) - k^2\varepsilon_r\Psi E_z\right)dxdy = \int_{\partial\Gamma}\frac{1}{\mu_r}\Psi\frac{\partial E_z}{\partial n}dl \qquad (4)$$

An appropriate boundary condition for the surface of the $\Gamma$ domain, $\partial\Gamma$, should be, defined in order to calculate the incident field in Equation (4) and to assure that the scattered field represents an outward-propagating (radiating) solution. The numerical code developed for this application is based on the so-called Bayliss and Turkel Radiation Boundary Condition (RBC). This type of RBC offers several advantages: (1) A scatterer with an arbitrary shape can be enclosed in a circular surface not far away from the origin; (2) The incident field for this geometry can be well characterized; and (3) Numerical implementation of this type of RBC requires low computing resources because this type of RBC is a local boundary condition. Considering the second order Bayliss and Turkell RBC Equation 4 becomes:

$$\int\int\left(\nabla\Psi\left(\frac{1}{\mu_r}\nabla E_z\right) - k^2\varepsilon_r\Psi E_z\right)dxdy - \int_{\partial\Gamma}\alpha\Psi E_z - \beta\frac{\partial\Psi}{\partial\phi}\frac{\partial E_z}{\partial\phi}\rho d\phi = \qquad (5)$$
$$\int_{\partial\Gamma}\Psi\left\{\frac{\partial E_z^{inc}}{\partial\rho} - \alpha E_z^{inc} - \beta\frac{\partial^2 E_z^{inc}}{\partial\phi^2}\right\}\rho d\phi$$

The coefficients $\alpha$ and $\beta$ from Equation (5) satisfy the defining equation for the second order Bayliss and Turkell RBC and they are:

$$\alpha = \frac{-jk - \frac{3}{2\rho} - \frac{3j}{8k\rho^2}}{1 - \frac{j}{k\rho}} \qquad (6)$$

$$\beta = \frac{-\frac{j}{2k\rho^2}}{1 - \frac{j}{k\rho}} \qquad (7)$$

The scattered field from Equation (5) can be written as:

$$E_z^s = E_z - E_z^{inc} \qquad (8)$$

where $E_z$ is the total field and $E_z^{inc}$ is the incident field.

Equation (5) was solved for $E_z$ in its matrix form:

$$[A_{mn}][(E_z)_n] = [b_m] \qquad (9)$$

where:

$$A_{mn} = \int\int\left(\frac{1}{\mu_r}\nabla\Psi_m\nabla\Psi_n - k^2\varepsilon_r\Psi_m\Psi_n\right)dxdy - \qquad (10)$$
$$\int_{\partial\Gamma}\left(\alpha\Psi_m\Psi_n - \beta\frac{\partial\Psi_m}{\partial\phi}\frac{\partial\Psi_n}{\partial\phi}\right)\rho d\phi$$

and $$b_m = \int_{\partial\Gamma}\Psi_m\left\{\frac{\partial E_z^{inc}}{\partial\rho} - \alpha E_z^{inc} - \beta\frac{\partial^2 E_z^{inc}}{\partial\phi^2}\right\}\rho \qquad (11)$$

The triangular elements have been used to divide the entire surface $\delta$. For this type of element the procedure to solve surface integral from Equations (11) is well known. This procedure implies two steps: 1) solving integrals in their closed form for each element of mesh; and 2) multiplying the numbers obtained in the first step by predefined parameters in order to obtain the global result. The evaluation of a surface integral in closed form becomes possible using a local-area system of coordinates. A similar procedure may be used for the evaluation of boundary integrals from Equations (10) and (11). These integrals may be evaluated in their closed form using linear basis functions spanning each boundary element. Quantities evaluated locally for each surface and boundary element are added to appropriate location in matrices $[A_{mn}]$ and $[b_m]$ using a connectivity matrix to identify the global indices.

A second step in the reconstruction algorithm in accordance with the present subject matter corresponds to computing the difference vector between measured magnitude and phase of the electric field, $E_m$ and $\Phi_{E_m}$, and the corresponding calculated $E_c$ and $\Phi_{E_c}$. This difference vector can be written as:

$$\begin{Bmatrix} E_m - E_c \\ \Phi_{E_m} - \Phi_{E_c} \end{Bmatrix} \quad (12)$$

A third step in the reconstruction algorithm in accordance with the present subject matter corresponds to constructing the Jacobian matrix:

$$J = \begin{bmatrix} \frac{\partial E_1}{\partial \varepsilon_1} & \frac{\partial E_1}{\partial \varepsilon_2} & \cdots & \frac{\partial E_1}{\partial \varepsilon_N} & \frac{\partial E_1}{\partial \sigma_1} & \frac{\partial E_1}{\partial \sigma_2} & \cdots & \frac{\partial E_1}{\partial \sigma_N} \\ \frac{\partial \Phi_{E_1}}{\partial \varepsilon_1} & \frac{\partial \Phi_{E_1}}{\partial \varepsilon_2} & \cdots & \frac{\partial \Phi_{E_1}}{\partial \varepsilon_N} & \frac{\partial \Phi_{E_1}}{\partial \sigma_1} & \frac{\partial \Phi_{E_1}}{\partial \sigma_2} & \cdots & \frac{\partial \Phi_{E_1}}{\partial \sigma_N} \\ \vdots & \vdots & \ddots & \vdots & \vdots & \vdots & \ddots & \vdots \\ \frac{\partial E_M}{\partial \varepsilon_1} & \frac{\partial E_M}{\partial \varepsilon_2} & \cdots & \frac{\partial E_M}{\partial \varepsilon_N} & \frac{\partial E_M}{\partial \varepsilon_1} & \frac{\partial E_M}{\partial \varepsilon_2} & \cdots & \frac{\partial E_M}{\partial \sigma_N} \\ \frac{\partial \Phi_{E_M}}{\partial \varepsilon_1} & \frac{\partial \Phi_{E_M}}{\partial \varepsilon_2} & \cdots & \frac{\partial \Phi_{E_M}}{\partial \varepsilon_N} & \frac{\partial \Phi_{E_M}}{\partial \varepsilon_1} & \frac{\partial \Phi_{E_M}}{\partial \varepsilon_2} & \cdots & \frac{\partial \Phi_{E_L}}{\partial \sigma_N} \end{bmatrix} \quad (13)$$

where M is the number of boundary measurement sites.

A fourth step in the reconstruction algorithm in accordance with the present subject matter corresponds to determining the perturbation vector by solving the matrix equation:

$$[J^T J + \lambda I] \begin{Bmatrix} \Delta \varepsilon_r \\ \Delta \sigma \end{Bmatrix} = [J^T] \begin{Bmatrix} E_m - E_c \\ \Phi_{E_m} - \Phi_{E_c} \end{Bmatrix} \quad (14)$$

where $J^T$ is the transpose of the Jacobian matrix, I is the identity matrix and $\lambda$ is a regularization parameter determined by combined Marquardt and Tikhonov regularization schemes.

A fifth step in the reconstruction algorithm in accordance with the present subject matter corresponds to updating the values of material properties ($\varepsilon_r$, $\sigma$) computed in the previous step and then, based on these values, computing new values for electric field at the measurements sites. Steps (2)-(5) are repeated until a stable solution is reached.

As is indicated in FIG. 2 the reconstruction algorithm in accordance with the present technology uses calibration data derived in a pre-processing step. Prior to collecting measured electric field for image reconstruction, an equipment calibration procedure is followed. This calibration procedure is needed to minimize several differences existing between the measurement system and the numerical models used, including the use of a the 3D imaging system and 2D numerical models; differences in transmission efficiency of antennas and connection cables; and differences in the antenna positioning.

Taking into account these differences, a multi-step calibration procedure was developed. The first step in the calibration procedure addresses homogeneous correction computation. This correction was computed using the following relations:

$$\text{Phase}_{cor} = \text{Phase}_{hom}^{measured} - \text{Phase}_{hom}^{computed} \quad (15)$$

$$\ln(E_{cor}) = \ln(E_{hom}^{measured}) - \ln(E_{hom}^{completed}) \quad (16)$$

where $\text{Phase}_{cor}$ is the phase correction, $\text{Phase}_{hom}^{measured}$ is the measured phase for a homogeneous medium, i.e. with no scatterer in place, $\text{Phase}_{hom}^{computed}$ is the computed phase for the homogeneous medium, $E_{cor}$ is the amplitude correction, $E_{hom}^{measured}$ is the measured electric field amplitude for the homogeneous medium, and $E_{hom}^{computed}$ is the computed electric field amplitude for the homogeneous medium. The quantities $E_{hom}^{computed}$ and $\text{Phase}_{hom}^{computed}$ are computed models previously described.

The next step in the calibration procedure is to apply the corrections determined using Equations (15) and (16) to the measured values, $E_{in\ hom}^{measured}$ and $\text{Phase}_{in\ hom}^{measured}$, obtained when a scatterer, i.e. a phantom, with or without inclusion, was in place. The calibrated values for the phase, $\text{Phase}_{in\ hom}^{calibrated}$ and the amplitude, $E_{in\ hom}^{calibrated}$, respectively, are:

$$\text{Phase}_{in\ hom}^{calibrated} = \text{Phase}_{in\ hom}^{measured} - \text{Phase}_{cor} \quad (17)$$

$$\ln(E_{in\ hom}^{calibrated}) = \ln(E_{in\ hom}^{measured}) - \ln(E_{cor}) \quad (18)$$

The calibrated values, $\text{Phase}_{in\ hom}^{calibrated}$ and $E_{in\ hom}^{calibrated}$, are computed for each of the microwave antennas in the microwave-imaging array and become the input data for the reconstruction algorithm.

An ultrasound image may be obtained by rotating a transducer in a complete circle relative to an object to be investigated. In actual practice, either the transducer or the object to be investigated, or, in some circumstances, both transducer and object may be rotated depending on physical practical considerations. As previously noted, a single transducer 17 as illustrated in FIG. 1, or, alternatively, plural transducers or a transducer array may be employed in order to decrease the time necessary to obtain the initial ultrasound image.

Figure 3:
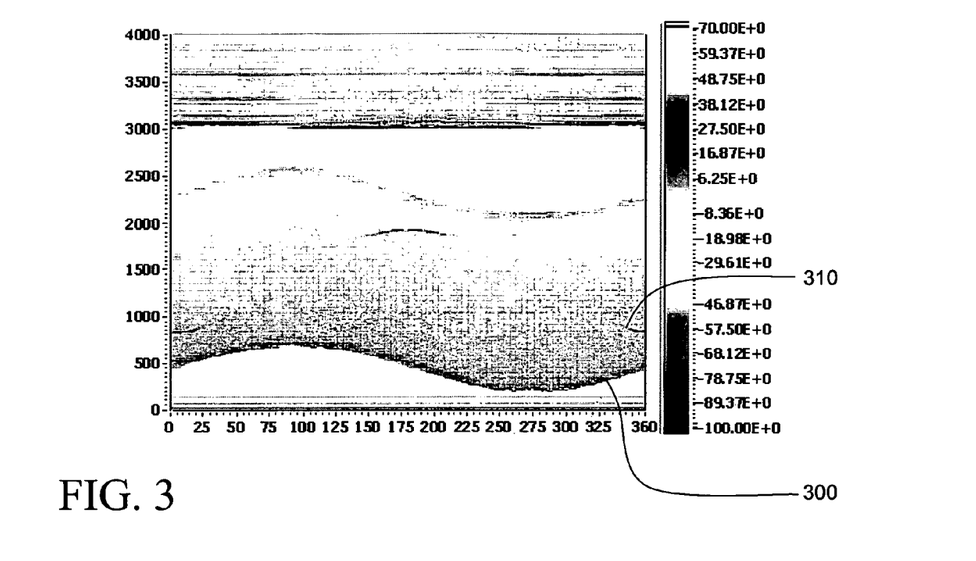
FIG. 3 is a representation of an ultrasonic image of a structure containing an inclusion that may be imaged using apparatus constructed in accordance with the present subject matter.
Figure 6:
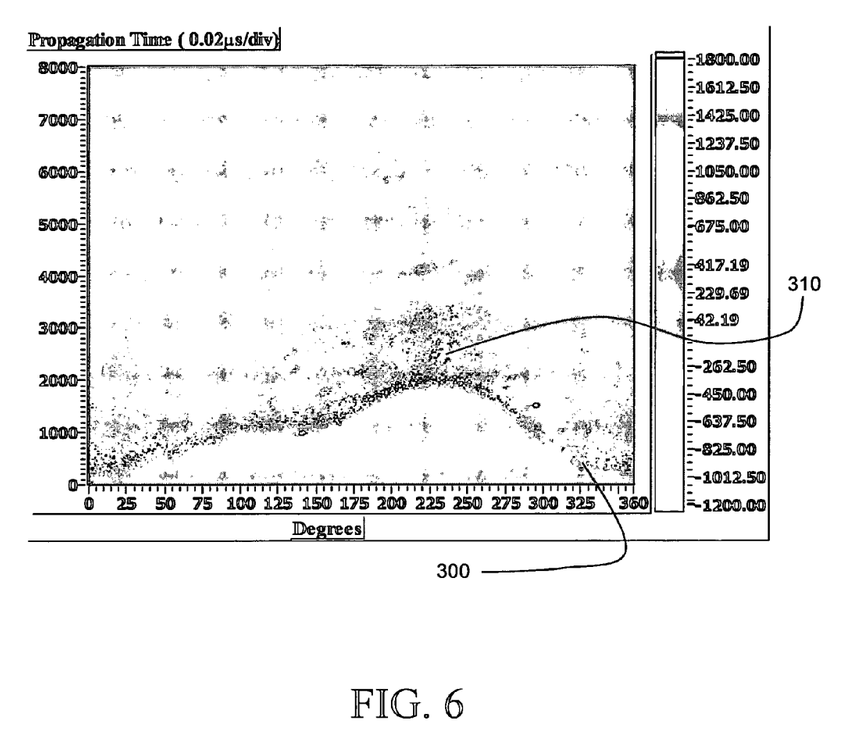
FIG. 6 is a representation of an ultrasonic image obtained on a human subject.
Figure 7A:
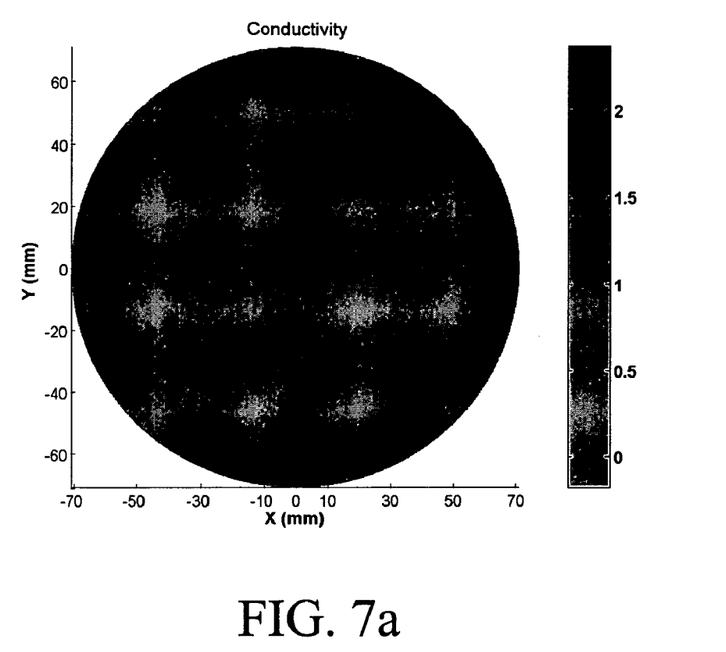
FIGS. 7a-7d respectively represent reconstructed images based on experimental data for a human patient: 7a) microwave conductivity image; 7b) microwave permittivity image; 7c) ultrasonically assisted conductivity microwave image; and 7d) ultrasonically assisted permittivity microwave image.
Figure 7B:
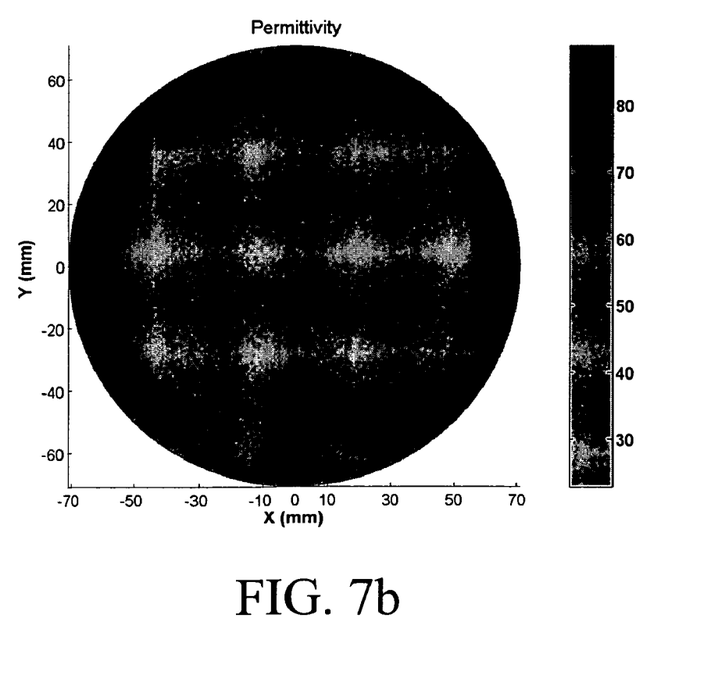
Figure 7C:
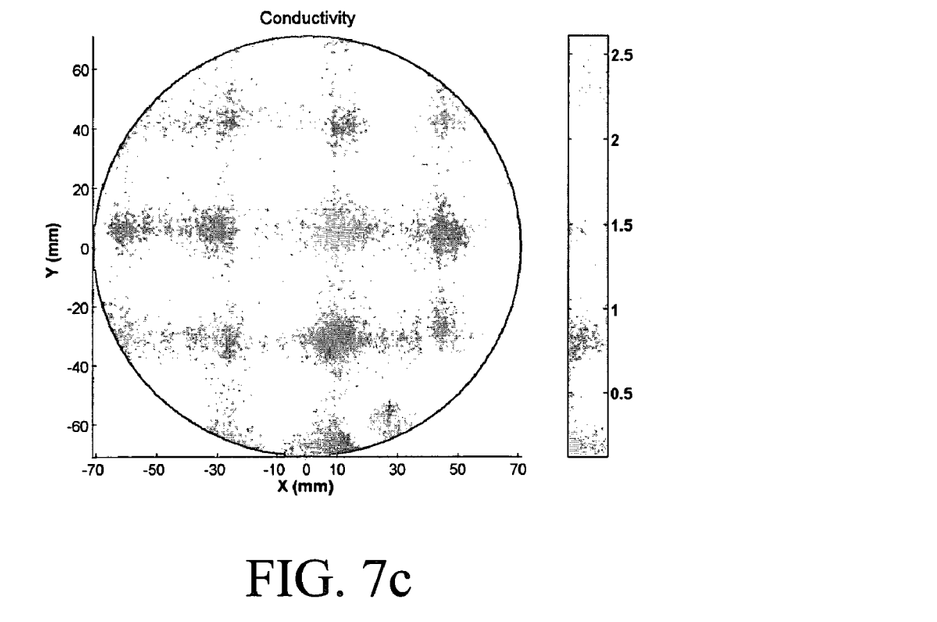
Figure 7D:
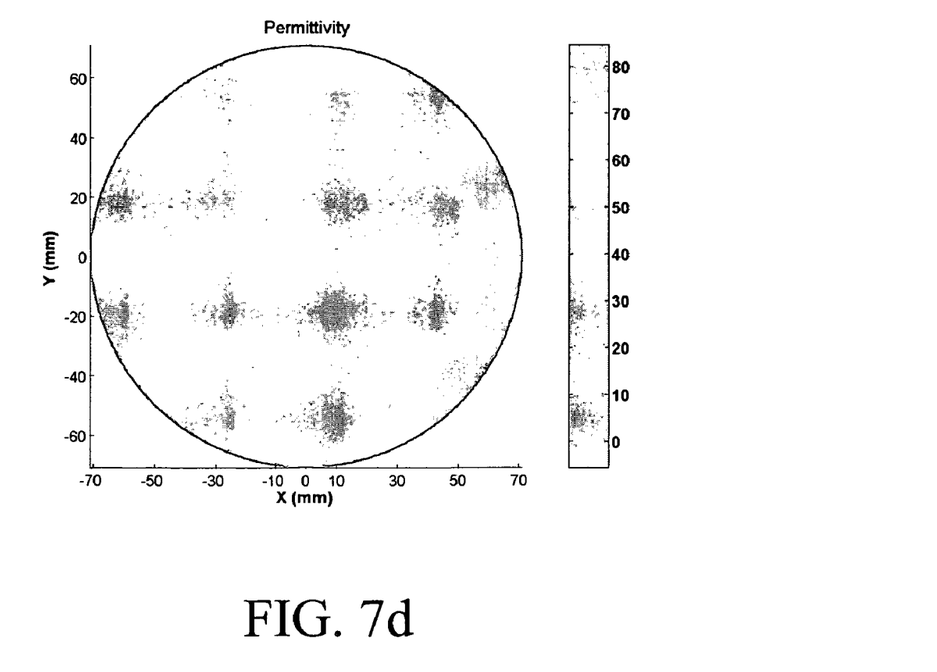

FIGS. 3 and 6 illustrate respectively images obtained for a phantom with a 1.2 mm inclusion and an image obtained for a human patient with benign tumor. At least two boundaries can be clearly identified in FIGS. 3 and 6. A first boundary 300 represents the interface between a phantom (or breast) and the coupling medium while the other boundary 310 represents the interface between a phantom (or breast) and an inclusion (or tumor) 310.

Figure 4:
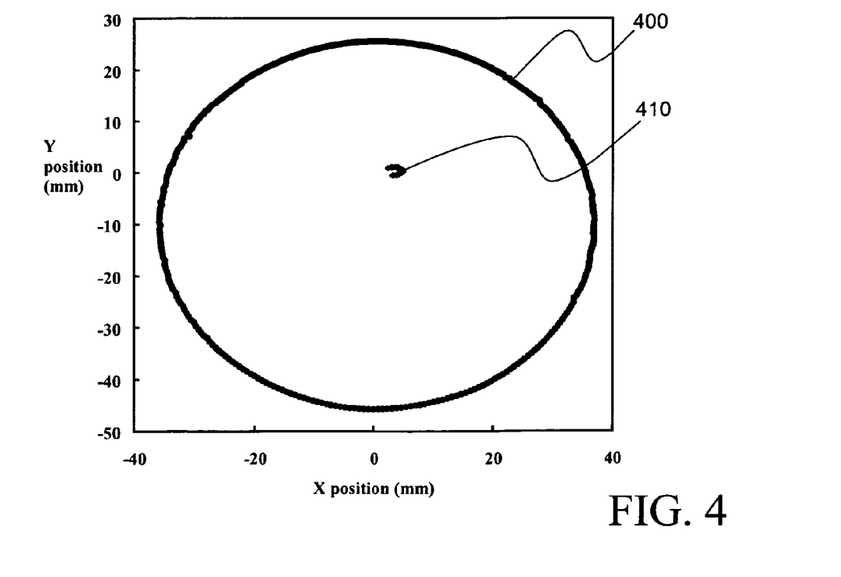
FIG. 4 is a polar representation of a determined profile for a phantom with a small inclusion.

The positions of interfaces may be determined from ultrasound images. FIG. 4 illustrates an image of the extracted edges of a phantom 400 with a 1.2 mm inclusion 410. Based on this information, a structured mesh for the finite element program used in image reconstruction may be generated. This mesh will have a higher density of nodes at detected edges. Calibration of collected microwave data may be performed using the mesh generated based on information extracted from an initial ultrasound image.

Finally, the reconstruction program is run with the distribution of initial values (initial guess) structured in the following three parts. First, the values of permittivity and conductivity in nodes corresponding to the coupling medium are known based on temperature and on salt concentration. Second, the values for electrical properties in the region of normal breast tissue are assigned to be close to the median values found in literature for normal breast tissue for the particular situation of the patient including, for example, the patient's age and whether the patient is post or pre menopausal. Third, the values from suspected tumor area are assigned to higher values than those corresponding to normal tissue. During the reconstruction process only the second and third values are to be determined.

Figure 5A:
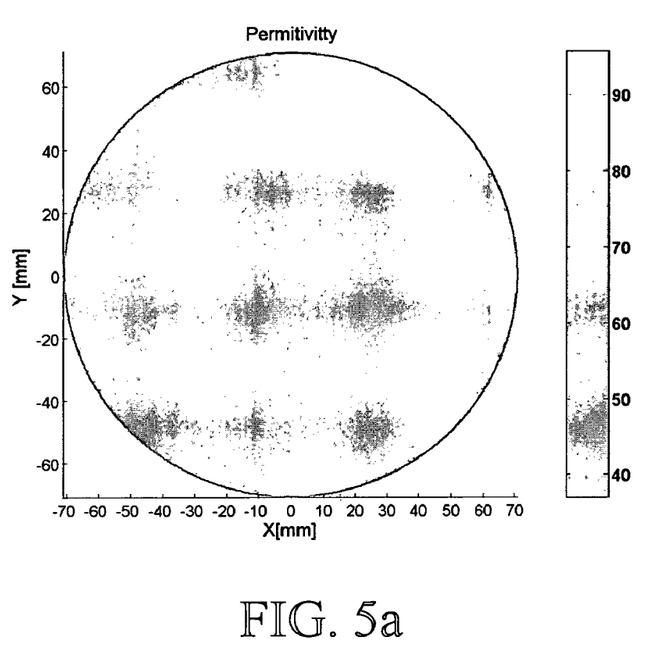
FIG. 5a is a microwave image that was not ultrasonically assisted and FIG. 5b represents an ultrasonically assisted microwave image.
Figure 5B:
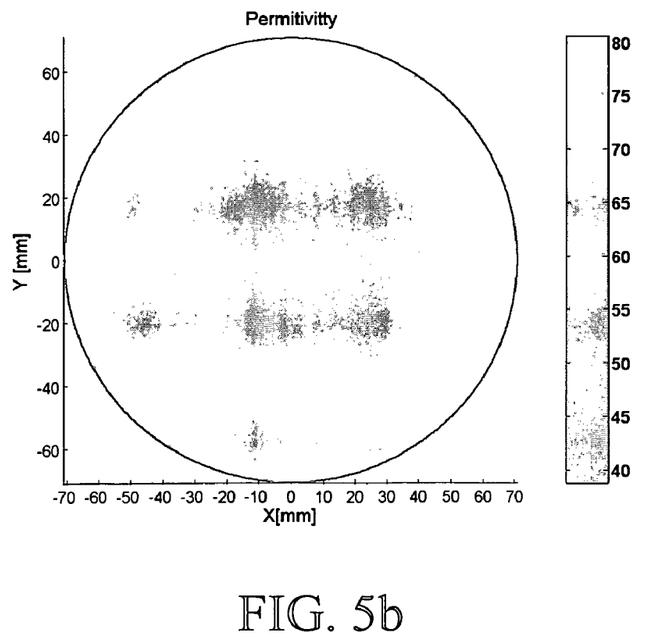

Microwave images obtained using the present technology have been found to show a better positioning and sizing of discontinuities together with a higher accuracy in electric properties reconstruction than microwave images using previously available technology. Differences between microwave images obtained with and without ultrasound assistance may be seen by comparison of FIGS. 5a and 5b. The permittivity images obtained without ultrasound assistance for a phantom with a 1.2 mm inclusion are illustrated in FIG. 5a. FIG. 5b illustrates an image obtained by applying the ultrasound assistance method in accordance with the present technology. The images obtained for a real patient with a benign tumor are illustrated in FIGS. 7a-7d. The images obtained using the method according to the present subject technology (FIGS. 7a and 7b) show clearly the presence of a tumor. The presence of multiple artifacts can be seen on the images illustrated in FIGS. 7c and 7d that obtained without ultrasound information.

While the present subject matter has been described in detail with respect to specific embodiments thereof, it will be appreciated that those skilled in the art, upon attaining an understanding of the foregoing may readily produce alterations to, variations of, and equivalents to such embodiments. Accordingly, the scope of the present disclosure is by way of example rather than by way of limitation, and the subject disclosure does not preclude inclusion of such modifications, variations and/or additions to the present subject matter as would be readily apparent to one of ordinary skill in the art.

What is claimed is:

1. A method for imaging an object under investigation, comprising the steps of:
   ultrasonically imaging at least a portion of an object under investigation;
   identifying at least one initial evaluation point for the object under investigation based on the step of ultrasonically imaging;
   after the step of ultrasonically imaging, microwave imaging at least the portion of the object imaged in the step of ultrasonically imaging; and
   reconstructing data obtained in the step of microwave imaging in based at least in part on the at least one initial evaluation point.

2. The method of claim 1, wherein the step of identifying comprises the step of identifying inhomogeneities within the portion of the ultrasonically imaged object.

3. The method of claim 2, wherein the step of identifying inhomogeneities comprises identifying variations in elastic properties within the ultrasonically imaged portion of the object.

4. The method of claim 3, wherein the step of identifying variations in elastic properties comprises identifying variations in acoustic impedance within the ultrasonically imaged portion of the object.

5. The method of claim 1, wherein the step of ultrasonically imaging comprises forming ultrasonic images based on second harmonic signal processing.

6. The method of claim 1, wherein the step of ultrasonically imaging comprises ultrasonically imaging at least one plane within an object under investigation and the step of microwave imaging comprises microwave imaging the at least one plane using an algorithm based on a Bayliss and Turkel Radiation Boundary Condition.

7. The method of claim 1, wherein the at least one initial evaluation point comprises an initial guess for the permittivity or conductivity of the object under investigation.

8. Imaging apparatus, comprising:
   an ultrasonic portion comprising an ultrasonic transducer and an ultrasonic transceiver coupled to said ultrasonic transducer;
   a microwave portion comprising a microwave radio frequency source, a multiplexer coupled to said microwave radio frequency source, and an antenna array coupled to said multiplexer; and
   a computer portion comprising a processor portion, a memory portion, and a display portion coupled to said multiplexer and said ultrasonic transceiver;
   said ultrasonic portion, said microwave portion and said computer portion configured to cooperate to produce a reconstructed microwave image of at least a portion of an object, said reconstructed microwave image being reconstructed based at least in part on at least one initial evaluation point determined from an ultrasonic image generated from said ultrasonic portion.

9. The imaging apparatus of claim 8, wherein the computer portion of the imaging apparatus is configured to cause the display portion to display inhomogeneities within the object and to cause the microwave portion to cooperate with the computer portion to produce the reconstructed microwave image of the inhomogeneities.

10. The imaging apparatus of claim 9, wherein the ultrasonic image comprises an image of a first cross section portion of the object and the reconstructed microwave image comprises a microwave image of at least said first cross section.

11. The imaging apparatus of claim 10, wherein the computer portion of the imaging apparatus is configured to cause the microwave portion to produce the reconstructed microwave image of at least a second cross section of the object on at least a first side of the of the first cross section.

12. The imaging apparatus of claim 11, wherein the computer portion of the imaging apparatus is configured to cause the microwave portion to produce the reconstructed microwave image of at least a third cross section of the object on at least a second side of the of the first cross section.

13. A method for reconstructing an image of a portion of an object, comprising the steps of:
   collecting first image data points from a portion of an object based on a first image producing technology;
   evaluating the first image data points to determine an initial evaluation point for selected characteristics of the portion of the object;
   collecting second image data points from a portion of the object using a second image producing technology; and
   reconstructing the image of the portion of the object using the second image data points in an iterative process and employing the initial evaluation point for the selected characteristics determined in the step of evaluating the first image data points as initial values for the iterative process,
   wherein the first image producing technology is an ultrasonic image producing technology and the second image producing technology is a microwave image producing technology.

14. The method of claim 13, wherein the selected characteristics comprise permittivity and conductivity.

15. The method of claim 13, wherein the iterative process comprises the steps of:

a) computing the electric field within the object at selected points;
b) computing a difference vector between electric field data at selected points and computed electric field data at selected points;
c) computing perturbation vectors of electric properties of the object;
d) re-computing the electric field based on new values of the electrical properties of the object; and
e) repeating steps b-d until a stable solution is reached.

* * * * *